US00PP12275P2

(12) United States Plant Patent
Goode, Jr.

(10) Patent No.: US PP12,275 P2
(45) Date of Patent: Dec. 11, 2001

(54) DIEFFENBACHIA PLANT NAMED 'CAMOUFLAGE'

(76) Inventor: Thomas Lee Goode, Jr., 1342 Deer Lake Cir., Apopka, FL (US) 32712

( * ) Notice: Subject to any disclaimer, the term of this patent is extended or adjusted under 35 U.S.C. 154(b) by 0 days.

(21) Appl. No.: 09/484,289

(22) Filed: Jan. 18, 2000

(51) Int. Cl.[7] ..... A01H 5/00
(52) U.S. Cl. ..... Plt./378

(58) Field of Search ..... Plt./378

*Primary Examiner*—Bruce R. Campell
*Assistant Examiner*—Annette Para
(74) *Attorney, Agent, or Firm*—C. A. Whealy

(57) ABSTRACT

A distinct cultivar of Dieffenbachia plant named 'Camouflage', characterized by its large leaves with attractive and unique variegation pattern; upright and outwardly arching growth habit; and freely clumping habit, full and dense plants.

2 Drawing Sheets

BACKGROUND OF THE INVENTION

The present Invention relates to a new and distinct cultivar of Dieffenbachia plant, botanically known as Dieffenbachia sp. and referred to by the cultivar name Camouflage.

The new Dieffenbachia is a naturally-occurring whole plant mutation of the Dieffenbachia sp. cultivar Panther, not patented. The new Dieffenbachia was discovered by the Inventor in a controlled environment in Apopka, Fla. as a single plant within a large population of plants of the cultivar Panther. The selection of this plant was based on its attractive and unique variegated foliage. Plants of the new Dieffenbachia and plants of the parent cultivar differ in leaf variegation pattern and leaf colors.

Asexual propagation of the new cultivar by cuttings and by tissue-culture at Apopka, Fla., has shown that the unique features of this new Dieffenbachia are stable and reproduced true to type in successive generations.

SUMMARY OF THE INVENTION

The following traits have been repeatedly observed and are determined to be the unique characteristics of 'Camouflage'. These characteristics in combination distinguish 'Camouflage' as a new and distinct cultivar:

1. Large leaves with attractive and unique variegation pattern.
2. Upright and outwardly arching growth habit.
3. Freely clumping habit, full and dense plants.

The cultivar Camouflage has not been observed under all possible environmental conditions. The phenotype may vary somewhat with variations in environment such as temperature, light intensity and/or fertilizer rate, without, however, any variance in genotype.

BRIEF DESCRIPTION OF THE PHOTOGRAPHS

The accompanying colored photographs illustrate the overall appearance of the new Dieffenbachia, showing the colors as true as it is reasonably possible to obtain in colored reproduction of this type. Colors in the photographs may differ slightly from the color values cited in the detailed botanical description which more accurately describe the actual colors of the new Dieffenbachia.

The photograph on the first sheet comprises a top perspective view of a typical plant of 'Camouflage'.

The photograph at the top of the second sheet comprises a close-up view of the upper surface of a typical leaf of 'Camouflage'.

The photograph at the bottom of the second sheet comprises a close-up view of the lower surface of a typical leaf of 'Camouflage'.

DETAILED BOTANICAL DESCRIPTION

The following observations, measurements and values describe plants of the new Dieffenbachia grown in 20-cm containers, in Apopka, Fla., under greenhouse conditions which closely approximate commercial Dieffenbachia production. Plants were described when they were about one-year old. Color references are made to The Royal Horticultural Society Colour Chart except where general terms of ordinary dictionary significance are used.

Botanical classification: Dieffenbachia sp. cultivar Camouflage.

Parentage: Naturally-occurring whole plant mutation of the Dieffenbachia sp. cultivar Panther, not patented.

Propagation:

*Type.*—By cuttings and by tissue-culture.

*Time to initiate roots.*—Summer: About 14 days at 32° C. Winter: About 21 days at 21° C.

*Time to produce a rooted liner.*—Summer: About 70 days at 32° C. Winter: About 84 days at 21° C.

*Root description.*—Thick, white fleshy roots with fine lateral roots.

Plant description:

*Appearance.*—Upright and outwardly arching.

*Plant height.*—About 100 cm.

*Plant width.*—About 100 cm.

*Stem length.*—About 40 cm.

*Stem diameter, at base of plant.*—About 6.4 cm.

*Stem color.*—146C to 146D with occasional darker green, 147A, streaks. Stems are generally not visible as the petiole wings clasp the stem.

*Branching habit.*—Freely clumping habit, tissue-cultured plants typically produce three to five offshoots. Full and dense plants.

*Foliage description.*—Length: Up to about 70 cm. Width: Up to about 35 cm. Shape: Lanceolate. Apex: Acuminate. Base: Cordate, sometimes slightly oblique. Margin: Entire. Aspect: Lamina on either side of the midrib are unequal in width resulting in a slight curving of the leaf blade towards the narrower side. Fully expanded leaves are orientated about 90° to the stem axis. Texture: Smooth. Midrib: Prominent on the lower surface. Primary veins: Recessed on upper surface and prominent on lower surface. Petiole length: About 20 cm. Petiole diameter: At apex: About 9.5 mm. At base: About 3.8 cm. Petiole wing length: About 15.25 cm. Color: Irregular variegation patterns. Background: There are two background colors, light green, 145C, which covers the center of the leaf and extends to about one third of the distance from the midrib to the margin. This light green color blends into a second darker green, 146C to 146D, background color which extends to the leaf margin. Islands/spots/blotches: There are three differently-colored and irregularly shaped islands/spots/blotches that are scattered randomly throughout the leaf blade. The most numerous and predominant areas are dark green, 147A, which can be described as larger islands and many smaller areas that are less than 1 mm in diameter. These dark green areas contrast sharply with the two background colors. Random bright green, 144A, irregular areas are fewer in number and are generally located at the junction of the lighter and darker background areas. The least noticeable blotches, 137B to 137C in color, are located randomly throughout the leaf blade. Midrib: Background, 193A, with numerous small dark green, 147A, scattered streaks. Primary veins: Color is similar to the color of the adjacent leaf blade. Petiole and petiole wing: 147B with thin darker green, 147A, streaks.

Inflorescence description: Inflorescence development was not observed on plants of the new Dieffenbachia used for this description.

Disease resistance: Resistance to pathogens common to Dieffenbachia has not been observed on plants of the new Dieffenbachia.

It is claimed:

1. A new and distinct cultivar of Dieffenbachia plant named 'Camouflage', as illustrated and described.

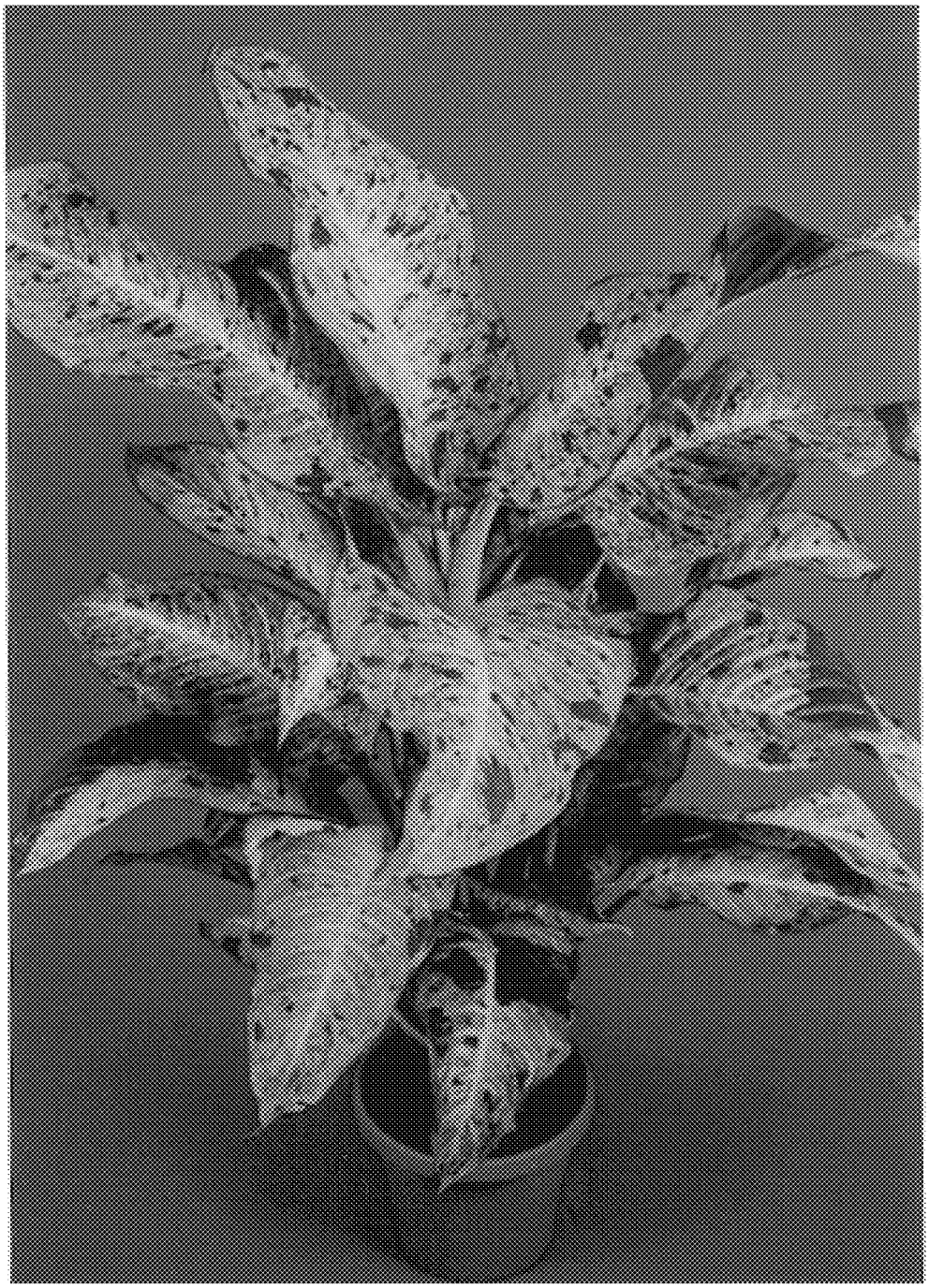

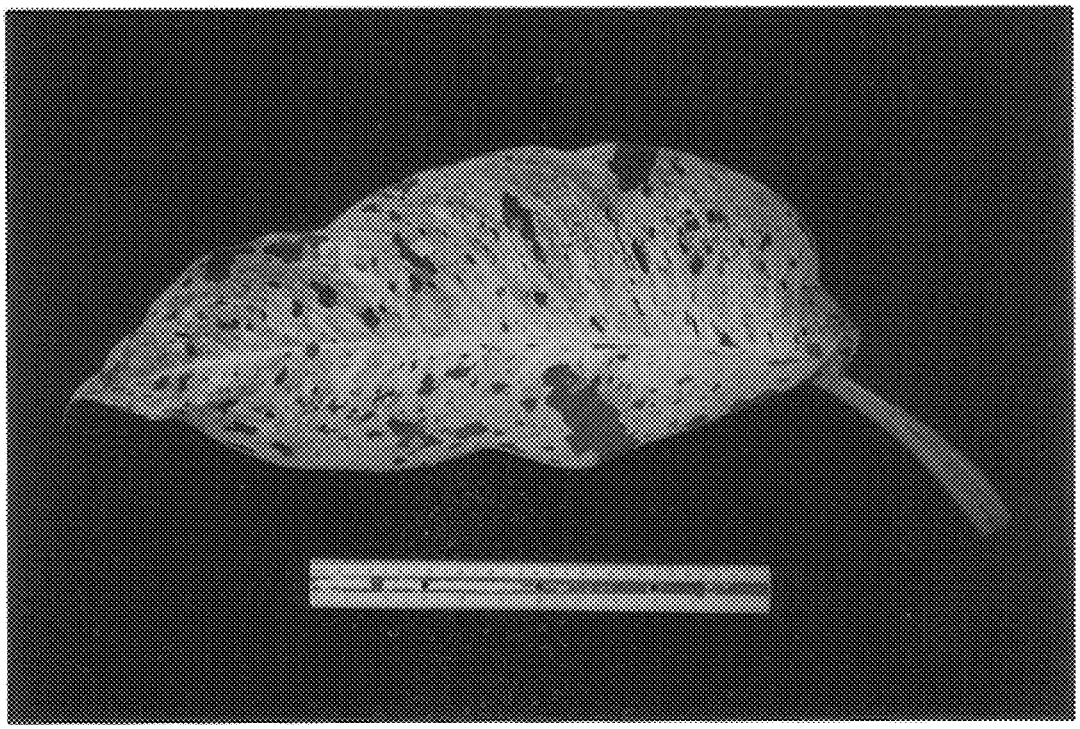
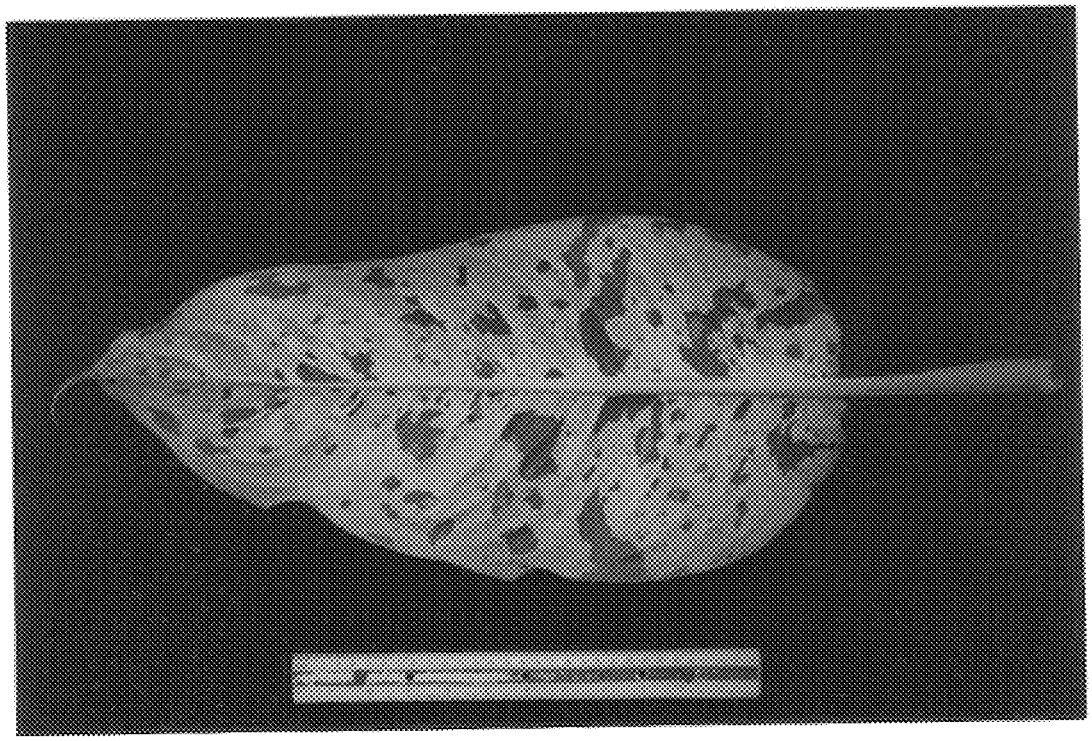

* * * * *